United States Patent [19]
Moczar et al.

[11] Patent Number: 5,910,490
[45] Date of Patent: Jun. 8, 1999

[54] USE OF OLIGOSACCHARIDES IN THE PREVENTION AND TREATMENT OF THE AGING OF TISSUES

[75] Inventors: Elemer Moczar, Gif-sur-Yvette; Ladislas Robert; Alexandre Robert, both of Santeny, all of France

[73] Assignee: ROC. S.A., Colombes, France

[21] Appl. No.: 08/592,317

[22] PCT Filed: Aug. 16, 1994

[86] PCT No.: PCT/FR94/01008

§ 371 Date: Feb. 16, 1996

§ 102(e) Date: Feb. 16, 1996

[87] PCT Pub. No.: WO95/05155

PCT Pub. Date: Feb. 23, 1995

[30] Foreign Application Priority Data

Aug. 17, 1993 [FR] France .................................. 93 10054

[51] Int. Cl.⁶ ........................ A61K 31/715; A61K 31/70; A61K 7/40
[52] U.S. Cl. .............................. 514/54; 514/53; 514/844; 536/123.1; 536/123.13
[58] Field of Search ................................ 514/53, 54, 844; 536/123.1, 123.13

[56] References Cited

U.S. PATENT DOCUMENTS

| | | | |
|---|---|---|---|
| Re. 28,781 | 4/1976 | Koenig et al. ............................ | 424/361 |
| 4,683,222 | 7/1987 | Stadler et al. ............................ | 514/42 |
| 4,895,838 | 1/1990 | McCluer et al. .......................... | 514/54 |
| 5,280,111 | 1/1994 | Shoji et al. ............................... | 536/4.1 |

FOREIGN PATENT DOCUMENTS

| | | |
|---|---|---|
| 0 133 170 | 2/1985 | European Pat. Off. . |
| 0 504 645 | 9/1992 | European Pat. Off. . |
| 550278 | 7/1993 | European Pat. Off. . |
| 2 609 397 | 7/1988 | France . |
| 62-267238 | 11/1987 | Japan . |
| 90/07516 | 12/1990 | WIPO . |

OTHER PUBLICATIONS

Editor Peter M. Collins, *Carbohydrates*, Chapman & Hall (London, New York), pp. 312, 336, 431, 461, 1987.
Collins & Ferrier. Monosaccharides: Their Chemistry and Their Roles in Natural Products. (John Wiley & Sons), p. 4, 1995.
Hronowski et al., *Carb. Res.*, vol. 219: 51–69, 1991.
Derwent Publications Ltd. Abstract JP A 2 265,458, Oct. 30, 1990, London.
Patent Abstracts of Japan, vol. 9, No. 32, Feb. 9, 1985 JP A 59 176 203.
Patent Abstracts of Japan, vol. 11, No. 167, May 28, 1987, JP A 62 000 412.
Patent Abstracts of Japan, vol. 12, No. 230, Jun. 29, 1988, JP A 63 023 808.

*Primary Examiner*—Howard C. Lee
*Attorney, Agent, or Firm*—Foley & Lardner

[57] ABSTRACT

Composition for the treatment or prevention of the symptoms of connective tissue ageing, characterized in that it contains one or more oligosaccharides with 2 to 5 oligosaccharide residues or a derivative of said oligosaccharide(s) containing a hydrophobic residue, with the proviso that one galactose residue be present in a non-reducing terminal position of said oligosaccharide(s).

28 Claims, 1 Drawing Sheet

ALDEHYDE FORM OF
MELIBIOSE (Melibiose - CHO)

CH$_2$-CHOH-CHOH-CHOH-CHOH-CHOH

Melibiose CHO + H$_2$N - (CH$_2$)$_6$ - NH$_2$ + OHC - Melibiose

↓ ↖—— 1,6-diaminohexane

Melibiose - CH = N - (CH$_2$)$_6$ - N = CH - Melibiose (unstable Schiff's base)

NaCNBH$_4$ ↓

[ Melibiose - CH$_2$ ] - NH - (CH$_2$)$_6$ - NH - CH$_2$ - Melibiose

MELIBIONITOL

Melibionitol - NH (CH$_2$)$_6$ - NH - Melibionitol dimelbionityldiaminohexane

USE OF OLIGOSACCHARIDES IN THE PREVENTION AND TREATMENT OF THE AGING OF TISSUES

BACKGROUND OF THE INVENTION

The present invention relates to a composition for the treatment or prevention of manifestations of aging containing oligosaccharides or derivatives of oligosaccharides having D-galactose in a non-reducing terminal position, these derivatives acting as modulators of the synthesis and/or the excretion of the elastase of fibroblasts.

It is known that the connective tissue in the dermis results from the biosynthetic activity of the fibroblasts which elaborate the extracellular matrix (Labat-Robert, J., et al., Elsevier Science Publisher B. V., 248: 386–393, 1990).

The extracellular matrix is composed of four families of macromolecules. These are the collagens and elastin which constitute the fibrous material of the dermis, the structural glycoproteins which provide for cohesion between the cells and the extracellular matrix and furnish the microfibrillary material of the elastic tissue, and the proteoglycans which provide for the hydration of the tissues and the control of molecular flow and interactions.

Elastin possesses a complex receptor in the membrane of the fibroblast cells which contains a 67 kD subunit which includes a binding site for the carbohydrates.

A. Hinek et al. (Science 239): 1539–1541 1988) showed that when the 67 kD subunit of the elastin receptor was immobilized on an affinity column in which the ligand was composed of elastin or peptides of elastin, lactose (1 mM) was capable of eluting this 67 kD protein, and that galactose was equally efficacious in displacing the binding of the 67 kD protein to the elastin.

On the other hand, oligosaccharides that do not contain galactose are not capable of permitting the elution of the 67 kD protein bound to the elastin affinity column.

The authors therefore concluded from this that the elastin receptor was a protein having properties of binding to galactosides.

It is also known that the elastins, in the soluble or insoluble state, are susceptible to hydrolysis by endoproteases, especially elastases.

Different classes of proteases and endopeptidases have been itemized and a review of these different endopeptidases and their properties has been published by Barrett et al., 1977 (Barrett, A. J. Eds., North Holland, Amsterdam).

The elastases are proteases and endopeptidases whose properties are beginning to be studied thoroughly. The following articles, the content of which can be incorporated into the present text by reference, describe these properties:

Bieth J. (1978) "Elastase: structure, function and pathological role". Front. of Matrix Biol. Cis.: 1–82, and Homsy, R. et al. (1988) "Characterization of human skin fibroblasts elastase activity". Journ. Invest. Dermatol. 91: 472–477.

The designation of an enzyme by the name elastase does not imply that this protease is specific for elastin. In fact, the elastases hydrolyse a wide variety of protein substrates, and leucocytic elastase for example is capable of cleaving practically all the macromolecules of the connective tissue (Robert, L. 1988, Path. Biol.; 36: 1101–1107).

These proteases of the elastase type are capable of degrading the elastic fibres of the tissues as well as, moroever, other constituents such as collagen fibres or glycoproteins, for example fibronectin. This type of phenomenon has been described among the phenomena of cellular aging; numerous studies have shown that the synthesis and accumulation of this type of enzyme increases during aging, and the following may be mentioned in particular:

Labat-Robert, J. et al., Ann. New York Acad. Sci. (1992), 673: 16–22,

Robert, J. Sang Thronrbose Vaisseaux (1991), 3: 267–330,

Robert, L. Pathol. Biol. (1988), 36: 1101–1107.

These same proteases and endopeptidases are also capable of degrading the matrix constituents of other organs, for example the elastin of the lungs, thus leading to pulmonary emphysema, or of degrading the elastic lamina of the arteries and the elastin and collagen of the veins, thus promoting the development of vascular diseases: atherosclerosis and ateriosclerosis of the arteries and varicose veins. All these pathologies undergo an increase in their frequency and severity with age.

Other endopeptidases of the same kind (Zn metalloendopeptidases) are capable of activating inactive angiotensin I to angiotensin II, which can trigger severe arterial hypertension.

Finally, the enkephalinases, other Zn endopeptidases of the same kind, interfere with the functioning of the enkephalins and, depending on the extent to which they are in excess, can lead to disturbances in brain function.

The common denominator of all these endopeptidases acting on different substrates and leading to very diverse pathologies is that they possess a Zn-containing active site and are all bound to the cell membrane.

In the description which follows, the case of the elastase of the fibroblasts of the skin will be discussed, but the physiopathological mechanism and the treatment principle which will be presented are also valid for the other endopeptidases and other pathologies of which the non-limiting listing was given above.

SUMMARY OF THE INVENTION

The present invention relates to compositions for the treatment or prevention of the manifestations of the aging of connective tissue, characterized in that they contain at least one oligosaccharide with 2 to 5 osidic residues, or a derivative of such an oligoside containing a galactose in a non-reducing terminal position.

The invention relates to a composition which is characterized in that it is used for the treatment of the manifestations of skin aging, when the oligosaccharides or their derivatives are combined with a vehicle that is compatible with a cosmetic, and preferably topical, administration.

The invention also relates to compositions for the treatment or prevention of the manifestations of accelerated aging in respect of the fibrous stroma of the connective tissue that accompany certain pathologies, especially cardiovascular pathologies and pulmonary emphysema, the said composition containing oligosaccharides or their derivatives which have a galactose in a non-reducing terminal position.

DETAILED DESCRIPTION OF PREFERRED EMBODIMENTS

Figure 1:
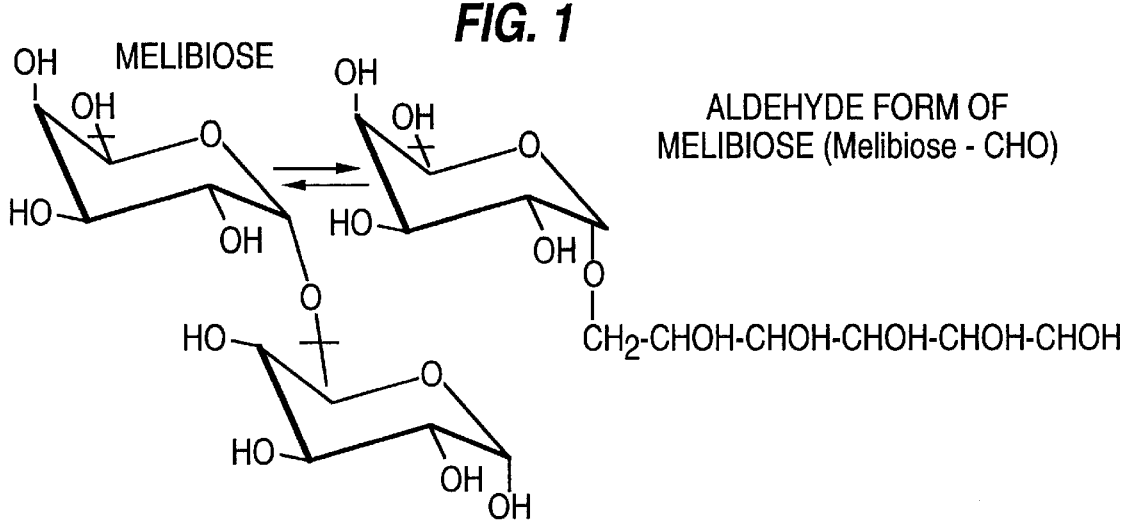

The oligosaccharides participating in the composition for the treatment or prevention of the manifestations of skin aging or of accelerated aging in respect of the fibrous stroma of the connective tissue are preferably lactose, melibiose, stachyose or derivatives of one of these sugars or a mixture of these.

The oligosaccharide derivatives that can participate in a composition according to the invention all contain a galactose residue in a non-reducing terminal position; they can fall within the categories mentioned below, in which the oligoside corresponds to the following general formula:

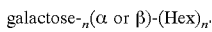

in which
n represents position 1, 2, 3, 4 or 6,
Hex represents a pentose or hexose linked in the α or β configuration,
n' is a number between 1 and 5;
a)—glycosides corresponding to the formulae:
(I) oligoside 1—O—R, in which R is a linear or branched alkyl residue with 1 to 18 carbon atoms,
(II) oligoside 1—O—R—O—1-oligoglycoside, in which R=$(CH_2)_{n'}$, n being between 2 and 10,
b)—an acylated osylamine according to one of the following formulae, in which the oligoside is preferably lactose, melibiose or stachyose:
acylated osylamine corresponding to one of the following formulae:
(III) oligoside 1—NH—CO—R, in which R is an alkyl residue with 2 to 18 carbon atoms, containing 0, 1 or 2 double bonds,
(IV) oligoside 1—NH—CO—R—CO—NH—1-oligoglycoside, in which R=$(CH_2)_{n'}$ n being between 2 and 8,
c)—an alkylamine acylated with an aldonic acid obtained by oxidation of an oligoside,
(V) oligoside—CO—NH—R, in which R has the same meaning as in the formula (III),
(VI) oligoside CO—NH—R—NH—CO—oligoglycoside, where R has the same meaning as in the formula (III),
d)—or a product of the reduction of the Schiff's bases which are formed by oligoside with aliphatic mono- or diamines, and corresponding to one of the following formulae:
(VII) Gal—$(Hex)_n$—X—HN—R,
(VIII) Gal—$(Hex)_n$—X—HN—R—NH—X-$(Hex)_n$—Gal, in which:
Hex is a hexose or pentose,
n=0, 1 or 2,
X=1—$NH_2$-hexitol, and
R has the same meaning as in (III).

All of these oligosaccharides or their derivatives described above have in common the feature of decreasing by at least 20% the synthesis and/or secretion of elastase in fibroblasts in culture.

This effect is manifested in the decrease in measurable enzymatic activity in the culture medium of these cells, as well as in the cells themselves.

The method used consists in culturing human skin fibroblasts under standard conditions and in determining the elastase activity of the culture by a colorimetric method, using a synthetic substrate (N-succinyltrialanylparanitroaniline.

Using this synthetic substrate, it was also possible to show that the biosynthesis of endopeptidases of the elastase type increases during successive passages of the fibroblasts, thus constituting an in vitro aging system in accordance with the model of Hayflick (1980, Cell Adding Inst. Annual Review of Gerontology and Geriatrics; Springer, N.Y. 1: 26–67); Labat-Robert J. et al. (1988, Expert Gerontol. 23: 5–18).

The enzymatic activity is essentially associated with the cell membrane and can be recovered after trypsinization of the fibroblasts in a soluble fraction.

Two to 10% of the total activity can be recovered in the culture media and the remainder is associated with the cell residues and can be solubilized using a detergent.

The present invention relates to the use of the oligosaccharides or their derivatives described above to control the biosynthesis and secretion of proteases of the elastase type from fibroblasts through the elastin receptor present on human fibroblasts especially skin fibroblasts, this control having the effect of preventing or treating the manifestations of skin aging, or those of accelerated aging linked to pathologies due, in particular, to the presence of an excess of endopeptidases.

In effect, as was stated above, the 67 kD subunit of the elastin receptor possesses a structure that reacts specifically with lactose or oligo- or polysaccharide structures containing galactose in a terminal position (Labat-Robert, J. et al., cited above, and Mecham, R. P. et al. 1989, Biochem. 28: 3716–3722).

The oligosaccharide derivatives participating in the composition of the invention can be synthesized either chemically, as will be explained later in the examples, or extracted from biological media, especially milk, blood or placenta, or alternatively from natural products such as honey which contains galactosides that are complementary for the preparation of the compositions of the invention (R. Siddiqui, in Advances in Carbohydrate Chemistry and Biochemistry, Ed: D. Horton, vol. 49, pp. 285–309).

The polysaccharides or their derivatives can thus be extracted by standard methods (Frontiers of Matrix Biology (1985), vol. 10, S. Kargar Edition), and then undergo either an enzymatic degradation or a chemical hydrolysis, and finally the relevant compound is separated either by saline precipitation or ion exchange chromatography or chromatography on Sepharose gel, or by any other suitable procedure.

The present invention also relates to the process for preparing a composition intended for the prevention or treatment of the effects of skin aging, characterized in that it comprises the incorporation into an acceptable vehicle for local administration of an oligosaccharide with 2 to 5 osidic residues comprising a galactose in a non-reducing terminal position, or of a derivative of such an oligosaccharide, which represents 0.5 to 6% by weight/volume of the said composition.

This composition can be used advantageously in dermatology and/or cosmetology for the treatment or prevention of the effects of skin aging.

Similarly, the invention relates to a process for preparing a composition intended for the prevention or treatment of the manifestations of accelerated aging in respect of the fibrous stroma of the connective tissue that accompany certain pathologies associated with an abnormal synthesis of elastase, in particular pulmonary emphysema, atherosclerosis and arteriosclerosis of the arteries and varicose veins or, finally, in the treatment or prevention of arterial hypertension when endopeptidases of the elastase type are responsible for the activation of angiotensin I to angiotensin II; this use is characterized by the incorporation into a composition, in combination with an acceptable pharmaceutical vehicle, of an oligosaccharide or oligosaccharide derivative containing a galactoside in a non-reducing terminal position.

When the oligosaccharide derivative comprises a hydrophobic residue, an advantageous vehicle can consist of liposomes, permitting the osidic fraction of the derivative to be presented at their surface.

In the detailed examples that follow, the effect is shown of lactose, melibiose, stachyose and their derivatives on the synthesis and secretion of elastase from human fibroblasts that have undergone 15 to 25 passages: the cells thus treated are cells that enter a senescence phase according to the model of Hayflick (reference see above) and thus constitute an in vitro aging model.

The decrease observed in the synthesis and secretion of elastase in such a system through the administration of the oligosaccharide derivatives of the invention is an index of the effect of these anti-aging compounds since, as we saw above, an increase in the synthesis and secretion of elastase are phenomena associated with the aging of these fibroblasts.

These examples are not restricted to an effect on the fibroblasts of the skin, but can be generalized to any type of fibroblast cells and other endothelial cells, smooth muscle cells and leucocytes possessing an elastin receptor in their membrane, this receptor comprising a 67 kD subunit that has an affinity for galactosides.

Materials and methods:

Human skin fibroblasts were obtained from skin biopsies taken in the course of mammary plastic surgery of a woman aged between 16 and 24 years.

The cells are cultured in Dulbecco's modified Eagle medium (DMEM) with 10% of foetal calf serum, 200 µg/ml of penicillin and 200 units/ml of streptomycin in an atmosphere of 90/10% oxygen/nitrogen in 35×10 mm NUNCLON-DELTA plastic bottles.

The experiments are carried out between the 18th and 21st passage, inasmuch as it is at this level that the elastase activity increases and reflects the state of senescence of the cells.

Twenty-four hours before the experiments, the medium is withdrawn and 1 ml of fresh DMEM medium was added with lactose at a final concentration of 10 mM.

After specified intervals of time, the medium was removed and the layer of cells rinsed twice with 1 ml of PBS (phosphate buffered saline) which was added to the medium.

The layer of cells was then treated with a fresh solution of trypsin (Worthington) at a concentration of 20 µg in 1 ml of PBS for 5 min at 37° C., followed by centrifugation at 100 g for 5 min at 4° C.

After decanting and rinsing with 1 ml of PBS, the cell residues are suspended in 1 ml of 0.1 M Tris-HCl buffer, pH 7.4, containing 0.1% of Triton x-100 and homogenized in a Potter homogenizer.

The supernatant of this suspension was used for the determination of the enzymatic activity associated with the cells.

The determination of the elastase type enzymatic activity was carried out by adding substrate N-succinyltrialanylparanitroanilide or N-suc-ala$_3$p-Na) at a concentration of 125 mM in dimethylformamide to an aliquot of cell extracts by the technique described in Bieth, J. 1978 (see above).

For the culture medium, 56 µl were added to 890 µl of 0.1 M Tris-HCl buffer, pH 7.8, and 10 µl of the substrate solution.

Fifty µl of the trypsinate or of cell residues were added to 940 µl of Tris buffer and to 10 µl of substrate.

The incubations are carried out at 37° C. for 3 h for the culture medium, and 1 h for the trypsinate and for the cell residue.

The optical density of the yellow colour which develops through the action of the enzyme on the substrate is read at 410 nanometres in a spectrophotometer.

All the experiments are carried out on 4 to 6 cultures in parallel, and mean values are compared statistically using the Student t-test.

The enzymatic activity (EA) is expressed in nM of substrate hydrolysed per hour and per $10^6$ cells, calculated as follows:

$$EA = \frac{OD \times v \text{ total}}{8.8 \times v \text{ sample} \times N \times T} \times 10^6$$

where:

OD is the optical density,

N is the number of cells in the reaction volume,

T is the incubation time, and 8.8 is the molar extinction coefficient corresponding to the OD of the molar solution of substrate in a cell of thickness 1 cm.

In the different examples that follow, the effect of galactose and its derivatives on the modification of the elastase activity of the fibroblasts was studied by measuring the modification of this activity by an elastin peptide: kappa-elastin (KE); this peptide was obtained by hydrolysis of elastin from the nuchal ligament of the ox, by alkaline hydrolysis in aqueous ethanol, by the technique described in Robert L. and Poullain N. (Etudes sur la structure de l'élastine et le mode d'action de l'élastase. I. Nouvelle méthode de préparation de dérivés solubles de l'élastine. [Studies on the structure of elastin and the mode of action of elastase. I. New method of preparation of soluble derivatives of elastin.] Bull. Soc. Chim. Biol. 45: 1317–1326 (1963)).

This peptide in effect has the property of being an agonist of the elastin receptor, that is to say its presence leads to an increase in the elastase activity of fibroblasts in culture.

Table 1 below shows the kinetics of the actions of kappa-elastin at 1 mg/lamella on the elastase activity of human fibroblasts at the twentieth passage as a function of the incubation time.

TABLE 1

| | INCUBATION TIME WITH KE | | | | |
|---|---|---|---|---|---|
| | 0 h | 2 h | 6 h | 24 h | 48 h |
| EA DMEM | 0.04 | 0.04 | 0.03 | 0.21 | 0.99 |
| EA TRYPS | 0.267 | 0.2 | 0.207 | 0.190 | 0.123 |

A large increase in the elastase activity is noted in the culture medium (secretion) after a latency period of 24 hrs. At the same time, the membrane activity in the trypsinate falls. It is thus seen that the increase in the activity in the medium could be connected with the release of the membrane enzyme into the medium.

EXAMPLE 1

Study of the action of lactose:

The concentration of lactose used is 10 mM or 3.6 mg/ml. Table 2 below shows the effect of 10 mM lactose on the elastase activity of human fibroblasts at the 21st passage and on its distribution between the free form, the membrane form (trypsinate) and the form associated with the cell (after Triton effect).

The activity is shown as the optical density of the hydrolysed substrate, multiplied by $10^3$/hr for $10^6$ cells.

A mean average of 4 parallel measurements on different cultures was calculated.

The distribution of the activity between the three compartments is shown as a percentage of the total, and similarly the inhibition by lactose is shown as a percentage of the equivalent activity in the absence of lactose.

TABLE 2

|  | Control | | Lactose | | |
| --- | --- | --- | --- | --- | --- |
|  | Activity | % of total | Activity | % of total | % |
| Total activity | 588.1 | 100 | 262.2 | 100 | 55 |
| Culture medium | 56.1 ± 7.6 | 10 | 18.8 ± 1.1 | 7 | 66 |
| Trypsinate | 359.5 ± 41.7 | 61 | 91.9 ± 31.7* | 35 | 74 |
| Cellular | 172.5 ± 16.8 | 29 | 151.5 ± 28.8 | 58 | 12 |

*$p < 0.05$ by comparing the control with lactose.

This table shows a reduction of 55% in the total activity, as well as a change in the distribution of the enzymatic activity in the three fractions.

The free enzyme measured in the culture medium decreases by 66% compared with the control culture and the enzyme associated with the membrane that can be released by the trypsin falls by 74%, whereas the residual (cellular) activity does not show a significant difference from the control.

This selective inhibition of the activities associated with the membrane and released into the medium modifies the distribution of the total activity.

In the control cultures, the major part of the total activity is associated with the cell membrane (61%) and can be released by trypsin; in the cultures treated with lactose, only 35% of the total activity is released by trypsin; 58% is associated with the cell residues.

It is thus seen that lactose has the effect of decreasing the synthesis of the enzyme and the release.

EXAMPLE 2

Study of the action of melibiose on the synthesis of elastase:

Melibiose is added to the culture medium at a concentration of 10 mM, that is to say 3.4 mg/ml, under the same conditions of culture as lactose.

Melibiose brings about a 60% decrease in the enzymatic activity in the medium relative to the control and an 80% decrease in the trypsinate, as well as a slight decrease in the cell pellet.

The total enzymatic activity is decreased by 50%.

EXAMPLE 3

Action of stachyose:

Stachyose is a tetrasaccharide which is prepared by the technique of M. L. Wolfrom and A. Thompson described in Methods of Carbohydrate Chemistry I, p. 368–369, Academic Press, 1962.

Stachyose was added to the culture medium at a concentration of 10 mM, that is to say 6.6 mg/ml.

It has the effect of decreasing the enzymatic activity in the trypsinate by 30% relative to the control, whereas it increases slightly in the medium.

In the presence of kappa-elastin at a concentration of 1 mg/ml, it decreases the enzymatic activity significantly in the medium (52%) relative to the effect of kappa-elastin alone.

In the trypsinate, an increase of 32% is observed, again relative to the effect of kappa-elastin alone.

The enzymatic activity in the pellets does not vary significantly.

EXAMPLE 4

Action of oleoyllactosylamine:

Oleoyllactosylamine is a compound corresponding to the formula X, and its synthesis is new.

a) Synthesis of oleoyllactosylamine:

1-Aminolactose reacts with oleoyl chloride to give lactobionyl-oleoylamine of the following formula:

$$\text{Galactose} \beta \text{—O—} \text{Glucose} \text{—NH—CO—} C_{13}H_{34}$$

3.3 g of lactosylamine are dissolved in 30 ml of methanol at 80° and 1.2 g of diethylamine are added. To this solution are added 4 g of oleoyl chloride, with stirring, at a temperature not exceeding 30° C.

The pH of the mixture is brought to 3 by adding HCl. The oleic acid is removed by extraction with heptane. The aqueous methanolic phase is passed successively through acidic and basic ion exchange columns and the solvents are driven off under vacuum.

The product obtained still contains about 20% of lactose. The oleoyllactosylamine can be purified on an octyl-Sepharose column. Rf=on silica (MeOH thin layer), 0.8 (chloroform/methanol 1:1, v/v).

b) Effect on senescent cultures of fibroblasts:

The oleoyllactosylamine is added at a concentration of 0.5 mM.

At this concentration, it produces a slight increase in the activity in the trypsinate and a drop in the cell pellets of about 20%.

EXAMPLE 5

Action of dimelibionityldiaminohexane:

a) Preparation of dimelibionityldiaminohexane:

This product was synthesized by a new technique described below. 374 mg melibiose (1.1 mM) and 116 mg (0.5 mM) of diaminohexane are dissolved in 5 ml of 0.2M phosphate buffer, pH 8, and to this are added 270 mg sodium cyanoborohydride (4.4 mM). The mixture is left to stand at room temperature for 11 days and then heated at 37° C. for 2 days. The solution is passed through an acidic ion exchanger (H+) and the column is washed with water.

The substance is then eluted with 0.5M ammonia solution and the solution is lyophilized. The yield is 200 mg of dimelibionityldiaminohexane. Rf on silica=0.2 (butanol/acetic acid:/water, h=1:1).

FIG. 1 shows the reaction scheme leading to the dimelibionityldiaminohexane derivatives.

b) Action of dimelibionityldiaminohexane on the enzymatic activity of cultures of human fibroblasts:

An increase is observed in the enzymatic activity in the medium, as well as a 40% decrease in the trypsinate relative to the control.

In the presence of kappa-elastin, the activity decreases by 71% in the medium, with no increase in the trypsinate.

In contrast, the activity recovered in the cell pellets increases slightly relative to the action of kappa-elastin alone, but does not shift the value of the control.

c) Comparison of the various effects:

Table 3 below summarizes the overall results obtained with the various galactoside derivatives on the elastase activity of human fibroblasts:

TABLE 3

ACTION ON ELASTASE ACTIVITY

| SUBSTANCE | TOTAL | DMEM | TRYPSINATE | C. PELLETS |
|---|---|---|---|---|
| LACTOSE | ↓27% | ↓30% | ↓70% | ↓30% |
| LACTOSE + KE | ↑13.5% | ↑20% | ↑50% | ↓30% |
| MELIBIOSE | ↓58% | ↓60% | ↓80% | ↓30% |
| MELIBIOSE + KE | ↑15% | ↓27% | ↑31% | ↑9% |
| STACHYOSE | ↓17% | ↑14% | ↓35% | — |
| STACHYOSE + KE | ↓17% | ↓56% | ↑32% | — |
| CARRAGEENAN | ↑28% | — | ↑66% | ↑30% |
| CARRAGEENAN + KE | — | ↓28% | ↑29% | — |
| L.O.AMINE | ↓15% | ↑44% | ↑61% | ↓19% |
| L.O.AMINE + KE | ↓27% | — | ↑41% | ↓32% |
| M.L.AMINE | ↑13% | ↓10% | ↓15% | ↓50% |
| M.L.AMINE + KE | ↑40% | ↓11% | ↑17% | ↓50% |
| MBA | ↓23% | ↑67% | — | ↓35% |
| MBA + KE | ↓7% | ↓60% | ↓20% | ↓23% |
| DMDAH | — | ↑67% | ↓53% | — |
| DMDAH + KE | ↑23% | ↑70% | ↓18% | ↑34% |
| MDH | ↑58% | ↓60% | ↑37% | ↑60% |
| MDH + KE | ↑54% | ↓80% | ↑14% | ↑56% |

LOAMINE = LACTOBIONYLOLEYLAMINE
MLAMINE = MYRISTOYLLACTOSYLAMINE
MBA = MELIBIONIC ACID
DMDAH = DIMELIBIONITOYLDIAMINOHEXANE [sic]
MDH = DIMELIBIITYLDIAMINOHEXANE The underlined derivatives are those that are mentioned in the examples above.

EXAMPLE 6

Effect of lactose and of melibiose in nude rats:

Two groups of rats are treated and compared, one with lactose or melibiose, the other with a placebo.

The rats are then irradiated with a dose of 3 MED (minimal erythematous dose).

The assay of elastase activity is measured in biopsies taken from the irradiated rats by the method described under Materials and methods.

We claim:

1. A method for treatment or for slowing the aging of connective tissue comprising:

administering to a subject in need thereof at least one oligosaccharide containing 2 to 5 osidic residues or a derivative thereof comprising a hydrophobic residue, the oligosaccharide or derivative thereof containing a galactose residue in a non-reducing terminal position.

2. A method according to claim 1, wherein said method inhibits membrane receptors for elastin which are involved in degradation of fibrous stroma of the connective tissue.

3. A method for the cosmetic treatment or the slowing of the manifestations of the aging of connective tissue comprising administering to a subject in need thereof at least one oligosaccharide containing 2 to 5 osidic residues or a derivative thereof comprising a hydrophobic residue, the oligosaccharide or derivative thereof containing a galactose residue in a non-reducing terminal position.

4. A method according to claim 1, wherein the oligosaccharide or said derivative is combined with a vehicle that is compatible with topical administration to form a dermocosmetic composition for treatment or slowing of the manifestation of skin aging.

5. A method according to claim 1, wherein the oligosaccharide possesses the following formula:

$$\text{galactose-}_n(\alpha \text{ or } \beta)\text{-}(X)_{n'}$$

in which n represents position 1, 2, 3, 4 or 6,

X represents a pentose or hexose linked in the α or β configuration, n' is a number between 1 and 5.

6. A method according to claim 5, wherein the oligosaccharide is melibiose.

7. A pharmaceutical composition for treating the aging of connective tissue comprising an oligosaccharide or an oligosaccharide derivative in an amount effective to decrease synthesis and/or secretion of elastase in fibroblasts by at least 20%, and a pharmaceutically acceptable excipient, wherein the oligosaccharide is an oligoside which corresponds to the formula (A):

$$\text{galactose-}_n(\alpha \text{ or } \beta)\text{-}(\text{Hex})_{n'} \qquad (A)$$

in which n represents position 1, 2, 3, 4 or 6,

Hex represents a pentose or hexose linked in the α or β configuration, n' is a number between 1 and 5, provided that, if the oligosaccharide is not substituted, it is not lactose, and the oligosaccharide derivative is selected from the group consisting of:

a)—a glycoside according to one of the following formulae:

(I) oligoside 1—O—$R^1$, in which $R^1$ is a linear or branched allyl residue with 1 to 18 carbon atoms, provided that if in the formula (A), Hex represents Gal and n equals 1, $R^1$ is other than ethyl or methyl, if the oligosaccharide is lactose, $R^1$ is other than an alkyl residue with 1 to 6 carbon atoms, (II) oligoside 1—O—$R^2$—O—1-oligoside in which $R^2$=$(CH_2)_m$, m being between 2 and 10, b)—an acylated osylamine according to one of the following formulae:

(III) oligoside 1—NH—CO—$R^3$, in which $R^3$ is an alkyl residue with 2 to 18 carbon atoms, containing 0, 1 or 2 double bonds, (IV) oligoside 1—NH—CO—$R^4$—CO—NH—1-oligoside, in which $R^4$ is $(CH_2)_p$, p being between 2 and 8, c)—an alkylamine acylated with an aldonic acid obtained by oxidation of an oligoside, (V) oligoside-CO—NH—$R^3$, in which $R^3$ has the same meaning as in (E) above, (VI) oligoside CO—NH—$R^3$—NH—CO-oligoside, where $R^3$ has the same meaning as in (III) above, or d)—a product of the reduction of the Schiff's bases which is formed by oligosides with aliphatic mono- or diamines, and corresponding to one of the following formulae:

(VII) Gal—$(\text{Hex})_q$—X—HN—$R^3$, (VIII) Gal—$(\text{Hex})_q$—X—HN—$R^3$—NH—X—$(\text{Hex})_q$—Gal, in which:

Hex is a residue of a hexose or pentose, q 0, 1 or 2,

X=residue of a hexitol or pentitol, and $R^3$ has the same meaning as in (III) above, wherein the oligosides of said formulae (I)–(VI) correspond to said formula A.

8. A composition according to claim 7, wherein said composition contains as active principle at least one oligosaccharide selected from the group consisting of melibiose, stachyose and mixtures of melibiose and stachyose.

9. A cosmetic composition for treating the aging of or for slowing connective tissue comprising an agent, present in an amount effective to decrease synthesis and/or secretion of elastase in fibroblasts by at least 20%, selected from the group consisting of melibiose and oligosaccharide derivatives containing 2 to 5 osidic residues and a galactose in a non-reducing terminal position, said derivatives being substituted with a hydrophobic radical, the derivatives being selected from the group consisting of:

a)—a glycoside according to one of the following:
(I) oligoside 1—O—$R^1$, in which $R^1$ is a linear or branched alkyl residue with 1 to 18 carbon atoms,
(II) oligoside 1—O—$R^2$—O—1-oligoside in which $R^2$=$(CH_2)_m$, m being between 2 and 10, b)—an acylated osylamine according to one of the following formulae:
(III) oligoside 1—NH—CO—$R^3$, in which $R^3$ is an alkyl residue with 2 to 18 carbon atoms, containing 0, 1 or 2 double bonds,
(IV) oligoside 1—NH—CO—$R^4$—CO—NH—1-oligoside, in which $R^4$=$(CH_2)_p$, p being between 2 and 8, c)—an alkylamine acylated with an aldonic acid obtained by oxidation of an oligoside,
(V) oligoside-CO—NH-$R^3$, in which $R^3$ has the same meaning as in (E) above,
(VI) oligoside CO—NH—$R^3$—NH—CO-oligoside, where $R^3$ has the same meaning as in (III) above, or d)—a product of the reduction of the Schiff's bases which is formed by oligosides with aliphatic mono- or diamines, and corresponding to one of the following formulae:
(VII) Gal—(Hex)$_q$—X—HN—$R^3$,
(VIII) Gal—(Hex)$_q$—X—HN—R—NH—X—(Hex)$_q$—Gal, in which:

Hex is a residue of a hexose or pentose,
n=0, 1 or 2,
X=residue of a hexitol or pentitol, and
$R^3$ has the same meaning as in (III), in which said oligoside of formulae (I) to (VI) corresponds to formula (A):

galactose-$_n$(α or β)—Hex)$_{n'}$ (A)

in which
n represents position 1, 2, 3, 4 or 6,
Hex represents a pentose or hexose linked in the α or β configuration,
n' is a number between 1 and 5.

10. A dermocosmetic composition comprising melibiose in an amount of between 0.5 and 6% weight/volume of said composition and a dermocosmetic acceptable carrier.

11. A process for preparing a composition according to claim 7 comprising:
incorporating an amount of between 0.5% and 6% weight/volume of said composition of said oligosaccharide or said oligosaccharide derivative thereof, into a vehicle suitable for local administration.

12. A pharmaceutical composition according to claim 7, wherein said oligoside of a) comprises lactose, melibiose or stachyose.

13. A pharmaceutical composition according to claim 7, wherein said oligoside of b) comprises lactose, melibiose or stachyose.

14. A cosmetic composition according to claim 9, wherein said oligoside of a) comprises lactose, melibiose or stachyose.

15. A cosmetic composition according to claim 9, wherein said oligoside of b) comprises lactose, melibiose or stachyose.

16. A process according to claim 11, wherein said oligosaccharide is present in an amount from 1 to 4% weight/volume based on the composition.

17. A method according to claim 1, wherein the oligosaccharide is selected from the group consisting of DMDAH and unsubstituted di-, tri- and tetrasaccharides containing a galactose residue in a non-reducing terminal position.

18. A method according to claim 17, wherein said method inhibits membrane receptors for elastin which are involved in degradation of fibrous stroma of the connective tissue.

19. A method according to claim 17, wherein the oligosaccharide is selected from the group consisting of lactose, melibiose, stachyose and DMDAH.

20. A method according to claim 3, wherein the oligosaccharide is selected from the group consisting of DMDAH and unsubstituted di-, tri- and tetrasaccharides containing a galactose residue in a non-reducing terminal position.

21. A method according to claim 20, wherein said oligosaccharide is combined with a vehicle that is compatible with topical administration to form a dermocosmetic composition for the treatment or the slowing of the manifestations of skin aging.

22. The method according to claim 20, wherein said oligosaccharide is selected from the group consisting of lactose, melibiose, stachyose and DMDAH.

23. A pharmaceutical composition according to claim 7, wherein said oligosaccharide is selected from the group consisting of DMDAH and unsubstituted di, tri- and tetrasaccharides containing a galactose residue in a non-reducing terminal position, provided that if said compound is an unsubstituted disaccharide, it is not lactose.

24. A pharmaceutical composition according to claim 23, wherein said oligosaccharide is selected from the group consisting of melibiose, stachyose and DMDAH.

25. A cosmetic composition according to claim 9, wherein said agent is selected from the group consisting of DMDAH and unsubstituted di-, tri- and tetrasaccharides containing a galactose residue in a non-reducing terminal position.

26. A cosmetic composition according to claim 25, wherein said agent is selected from the group consisting of lactose, melibiose, stachyose and DMDAH.

27. A process for preparing a composition according to claim 23 comprising:
incorporating an amount of between 0.5% and 6% weight of said oligosaccharide based on the volume of said composition, into a vehicle suitable for local administration.

28. A process according to claim 27, wherein said oligosaccharide is present in an amount from 1 to 4% weight/volume based on the composition.

* * * * *

UNITED STATES PATENT AND TRADEMARK OFFICE
CERTIFICATE OF CORRECTION

PATENT NO. : 5,910,490

DATED : June 8, 1999

INVENTOR(S) : Moczar et al.

It is certified that error appears in the above-identified patent and that said Letters Patent is hereby corrected as shown below:

Column 11, line 4, before "the aging of" insert --slowing--.

Column 11, line 8, before "oligosaccharide" insert --of--.

Column 12, line 47, delete "according to claim 9" and insert --for treating or for slowing the aging of connective tissue comprising an agent, present in an amount effective to decrease synthesis and/or secretion of elastase in fibroblasts by at least 20%--

Signed and Sealed this

Thirty-first Day of August, 1999

*Attest:*

Q. TODD DICKINSON

*Attesting Officer*     *Acting Commissioner of Patents and Trademarks*